United States Patent [19]

Cort et al.

[11] 4,285,858
[45] Aug. 25, 1981

[54] VASOPRESSIN ANALOGS

[75] Inventors: Joseph H. Cort, New York, N.Y.; Alan Fischman, New Haven, Conn.

[73] Assignee: Mt. Sinai School of Medicine of the City University of N.Y., New York, N.Y.

[21] Appl. No.: 89,510

[22] Filed: Oct. 30, 1979

[51] Int. Cl.$^3$ .................. C07C 103/52; A61K 37/00
[52] U.S. Cl. .............................. 260/112.5 R; 424/177
[58] Field of Search ................ 260/112.5 R; 424/177

[56] References Cited

U.S. PATENT DOCUMENTS

| | | | |
|---|---|---|---|
| 3,497,491 | 2/1970 | Zaoral et al. | 424/177 |
| 3,558,590 | 1/1971 | Cort et al. | 424/177 |
| 3,980,631 | 9/1976 | Prochozka et al. | 424/177 |

OTHER PUBLICATIONS

Cort et al., Molecular Endocrinology, 1977, 337–349.
Cho et al., Thrombosis et Diathesis Haemoirhagica 11, 1964, 372–392.
Cash et al., Clin. Sci. Molec. Med. 54, 403–409, 1978.
Prowse et al., Brit. J. Haematol 41, 1979, 437–447.
Capitanio, Lancet 1977, 869–872.
Lowe et al., Lancet 1977, 614–615.
Cort et al., Kidney Internat. 8, 1975, 292–302.
Gisin, Anal. Chim. Acta 58, (1972), 248–251.
Jost, K., Collect. Czech. Chem. Commun. 36, 218–233, 1971.
Schröder et al., "The Peptides", vol. II, (1966), 374–375.

Primary Examiner—Delbert R. Phillips
Attorney, Agent, or Firm—Brumbaugh, Graves, Donohue & Raymond

[57] ABSTRACT

Novel vasopressin analogs having the general schematic formula:

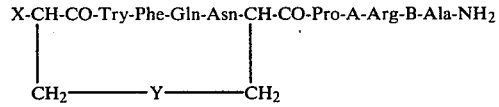

wherein X is selected from the group consisting of H and NH$_2$ and Y is selected from the group consisting of —S—S—, —CH$_2$S— and —SCH$_2$— and A=L when B=D and A=D when B=L and a method of treatment using these compounds to increase the level of Factor VIII and plasminogen activator in a subject's blood.

6 Claims, No Drawings

VASOPRESSIN ANALOGS

BACKGROUND OF THE INVENTION

This invention relates to a group of novel vasopressin analogs and methods of treatment using these compounds to increase the level of Factor VIII and Plasminogen activator in the blood.

Plasminogen activator (PA) is one of the substances in the fibrinolytic system which leads to the conversion of plasminogen to plasmin, the enzyme which lyses fibrin and thereby limits blood clotting. Factor VIII (F-VIII) is a blood factor which aids in the clotting of blood by causing prothrombin to be converted to thrombin, which in turn causes fibrinogen to be converted to fibrin. Some mammals including humans do not have any F-VIII or do not have sufficient amounts of F-VIII to clot their blood in a normal time period. This is due to a hereditary disease called hemophilia and is marked by a tendency towards bleeding and hemorrhaging. Many varieties of this disease exist but all involve defects of the clotting mechanism of the blood. A related blood clotting disease is von Willebrand's disease in which bleeding time is prolonged and the patient has a low level of anti-hemophilia globulins (AHG).

It has been known since 1961 (Schneck, A. S. von Kaulla, K. N., Neurology ii:959; Cho, M. H. and Choy. W., Thrombosis et Diathesis Haemorrhagica 11:372, 1964) that two pressor, vasoconstrictor hormones, adrenaline and vasopressin, can increase the blood levels of both PA and F-VIII in mammals (Cash, J. D., Gader, A. M. A., Mulder, J. L. and Cort, J. H., Clin.-Sci.Molec.Med. 54:403, 1978 and Prowse, C. V., Sas. G., Gader A. M. A., Cort. J. H. and Cash, J. D. Brit. J. Haematol. 41:437, 1979). The initial mechanism of action for this effect was considered to be a mechanical "squeezing" on the vascular endothelial cells considered to be the source of the F-VIII and PA. This theory was proven to be invalid when later studies (Cf. references above) showed that other pressor substances such as angiotensin II and oxytocin had no effect on increasing F-VIII and PA in blood and vasopressin-related peptides such as arginine-vasotocin, in equipressor doses, were far less active. In addition, non-pressor analogs of vasopressin such as 1-desamino-[8-D-ARG]-vasopressin (dDAVP-desmopressin) and 1-desamino-6-monocarba-[8-D-Arg]-vasopressin (dCDAVP) both had highly potent and prolonged effects on F-VIII and PA release.

Compounds such as desmopressin have been used in the treatment of hemophilia A and B and von Willebrand's disease. It increases low levels of F-VIII toward normal and allows surgery without administration of exogenous F-VIII plasma fractions (anti-hemophilia globulins=AHG) (Mannucci, P. M., Ruggeri, Z. M., Pareti, F. I. and Capitanio, A., Lancet i:869, 1977). The clinical use of desmopressin, however, is complicated by the pronounced and long-acting antidiuretic action of the analog which has resulted in undesired water retention by the patients (Lowe, G., Pettigrew, A., Middleton, S., Forces C. D., Prentice, C. R. M., Lancet ii:614 (1977).

SUMMARY OF THE INVENTION

It has now been found that a series of vasopressin analogs (herein sometimes referred to a peptide) can be synthesized which produce significant and prolonged increases in Factor VIII and PA in mammals without undesirable vasoconstriction or anti-diuretic side effects. The vasopressin analogs of this invention have the schematic formula:

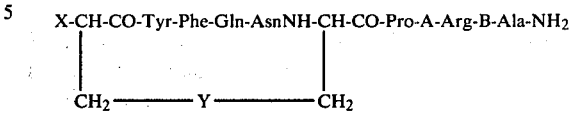

wherein X is selected from the group consisting of H and $NH_2$ and Y is selected from the group consisting of $-S-S-$, $-CH_2S-$ and $-SCH_2-$ and $A=L$ when $B=D$ and $A=D$ when $B=L$. All residues in the analogs of this invention have an L configuration unless otherwise indicated in the formula.

While this invention is not to be limited to any theory, we believe that the feature of the analog series responsible for the useful biological properties exhibited by these compounds is the alanine-amide (Ala—$NH_2$) in the C-terminal position of the analog. In standard vasopressin compounds the C-terminal sequence is Gly—$NH_2$.

The compounds of formula I can be administered intravenously and intranasally to mammals, suffering from hemophilia (types A and B), von Willebrand's disease and those in the thrombotic state. The compounds can also be administered to healthy blood donors to increase the level of F-VIII in the donor's blood. This is done in order to increase the yield of these important factors from volunteer's blood in order that F-VIII can be concentrated for use in treating hemophiliacs and other subjects suffering from clotting and related blood disorders. It is believed that these compounds also increase the level of PA in the blood.

The vasopressin analogs were synthesized by the solid phase method preferably using benzhydryl-amine resin, protected amino acid residues and an automatically programmable synthesizer. Liquid hydrogen fluoride, preferably in all Teflon* equipment, was used to remove the intermediate and final products from the resin phase. The methods of synthesizing the amino acid residue S-(4-methylbenzyl)-beta-mercaptopropionic acid is novel as well as the method of preparing the (1-desamino-1 monocarba-[9-D-Ala-$NH_2$]-arginine)-vasopressin and (1-desamino-6 monocarba-[9-D-Ala-$NH_2$]-arginine)-vasopressin.

*Teflon is the registered trademark of Dupont for polytetrafluoroethylene.

S-(4-methylbenzyl)-beta-mercaptopropionic acid (I) was prepared by reacting

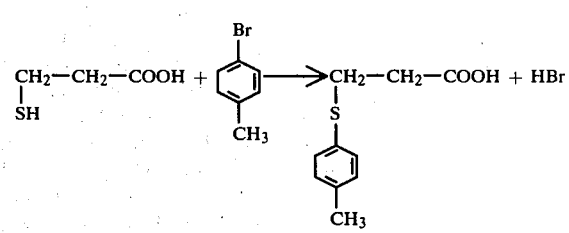

The (1-desamino-1-monocarba-[9-D-Ala-$NH_2$]-arginine) and (1-desamino-6-monocarba-[9-D-Ala-$NH_2$]-arginine)-vasopressin analogs were prepared by the solid phase method using benzhydrylamine resin, an automatically programmable synthesizer and the protected amino acid residues N-t-Boc-S-beta-ethoxycarbonylbutylcysteine and N-t-Boc-S-gamma-methoxycarbonyl-propylcysteine, respectively. Although this method of coupling amino acid residues using the solid phase method is known for the other amino acid residues used in this invention, prior to the work on this invention it had not been used with amino acid residues containing thio-ether bridges. Previously amino acid residues were coupled and cyclized using a reaction in solution (see U.S. Pat. Nos. 3,497,491 and 3,558,590).

The vasopressin analogs of this invention were tested for antidiuretic and pressor effects by intravenous injection into anesthetized rats using techniques described in Cort, J. H., Schück, O., Stribrna, J. Skopkova, J., Jost. K., Mulder, J. L., Kidney Internat. 8:292,1975. The increase in Factor VIII after administration were analyzed in male canine citrated plasma. The Factor VIII were estimated by both the classical clotting assay (F-VIII(C)) and by radioimmunoassay (F-VIII(RIA)), both described in Prowse, C. V., Sas, G., Gader, A. M. A., Cort, J. H., Cash, J. D., Brit. H. Haematol. 41:437, 1979. The vasopressin analogs are suitable for administration to mammals by intravenous or subcutaneous injection containing 100 $\mu$g to 1 mg peptide/ml. The intravenous or subcutaneous doses would be in the range of 0.02 to 1.0 $\mu$g/kg. The intranasal dose range would be ten times the former dose.

DETAILED DESCRIPTION OF PREFERRED EMBODIMENT

Many of the protected amino acid residues useful in synthesizing the preferred compounds of this invention are commercially available, for example, from VEGA Biochemicals, Inc., Tucson, Ariz. or Chemical Dynamics Inc., South Plainfield, N.J. The commercially available residues were checked for purity by thin layer chromatography (TLC) before use. Other useful amino acid residues such as S-(4-methylbenzyl)-beta-mercaptopropionic acid, N-t-Boc-S-beta ethoxycarbonylbutylcysteine and N-t-Boc-S-gamma-methoxycarbonylpropylcysteine were not commercially available and were synthesized for use in making the vasopressin analogs. The abbreviation t-Boc is used herein as accepted abbreviation for t-butyloxycarbonyl. The purity of the amino acid residues which were synthesized in the laboratory were determined by TLC, elemental analysis, NMR and melting point.

The amino acid residues as described above were used to synthesize the novel vasopressin analogs using benzhydrylamine-HCl in the VEGA 96 automatic programmable synthesizer manufactured by VEGA Biochemicals Inc. The C-terminal protected residue is reacted with benzhydryl-amine resin and then other residues are coupled to it one at a time by shaking and washing in organic solvents. Suitable solvents for the purpose are among others $CH_2Cl_2$ (methylene chloride) and dimethylformamide (DMF), isopropanol and mixtures thereof. The efficiency of the coupling at each step of the synthesis was monitored using picric acid according to the standard procedure described in Gisin, B. D., Anal. Chim. Acta 58,248 (1972). The resulting vasopressin analog was removed from the benzhydrylamine-HCl resin using hydrogen fluoride. The solution containing the end product was freeze dried and chromatographed to isolate the desired product which was checked for purity by TLC and analyzed for amino acids. Among suitable TLC solvent systems are mixtures of butanol, acetic acid, water, pyridine, and ethyl acetate.

The vasopressin analogs were injected intravenously into normal male dogs anesthetized with sodium pentothal. Blood was withdrawn from each dog after 30, 60 and 120 minutes and analyzed for F-VIII. Rats were also rested for antidiuretic and pressor activity due to the vasopressin analogs of this invention.

The following examples are not meant to limit the invention but serve to further illustrate and explain the preferred methods employed in synthesizing and testing the vasopressin analogs of this invention.

Examples 1–3 illustrate the synthesis of protected residues which were not commercially available and which were used in preparing some of the vasopressin analogs. The syntheses disclosed in Example 1 is a novel method of preparing the S-(4-Methylbenzyl)-beta-mercaptopropionic acid amino acid residue.

EXAMPLE 1

Preparation of S-(4-Methylbenzyl)-beta-mercaptopropionic acid

A solution of betamercaptopropionic acid (5.3 g, 50 mMol) in water (95 ml) was diluted with absolute ethanol (80 ml) and triethylamine (15 ml). While this solution was mechanically stirred and cooled with an ice bath, a solution of 4-methylbenzyl bromide (9.4 g) in ethanol (80 ml) was added over a period of 15 minutes. The ice bath was removed and the reaction mixture was stirred at room temperature for 2.5 hours. The mixture was then concentrated in vacuo and the residue was suspended in water (100 ml). As the pH of the suspension was adjusted to 10, the residue dissolved. The resulting solution was extracted three times with di-ethyl ether and the aqueous phase was acidified to pH 1 with concentrated HCl. An oily residue separated. The mixture was then exhaustively extracted with di-ethyl ether, the ether extracted was dried over $MgSO_4$ and concentrated to an oil. The latter solidified on standing and the solid residue was recrystallized from ethyl acetate-liquid petroleum. The yield was 7.9 g (75%), m.p. 75.8° C., NMR ($CDCl_3$) 11.5 (s, 1H), 7.09 (q, 4H), 3.67 (s, 2H), 2.60 (m, 4H), 2.30 (s, 3H).

EXAMPLE 2

Preparation of N-t-Boc-S-beta-ethoxycarbonylbutylcysteine

Ammonia was condensed and collected in a 3-neck round bottom flask in a dry ice/acetone bath until about 300 ml had collected. Solid sodium was added until a permanent blue color developed. A second flask containing 5 g (41 mMol) of cystine was then attached to one neck of the 3-neck flask and approximately 200 ml of the liquid $NH_3$ was distilled. Solid Na was added to the reaction mixture until the blue color persisted. The hemi-Cys became gelatinous and dissolved only with mechanical stirring. $NH_4Cl$ was added until the blue color disappeared. 4-bromobutyric acid ethyl ester (Merck) (12 g=61 mMol) was added and the mixture was stirred for 5 minutes in an ice bath. Nitrogen was bubbled through the mixture to drive off the ammonia, and then the flask was evacuated using a vacuum pump. The residue was dissolved in 10 ml 10% acetic acid. 50 ml distilled water was added and the pH of the mixture was adjusted to 6 using a glass electrode. At pH 6.5 the product dissolved and at pH 6.0 it precipitated as a white powder. The mixture was left at 4° C. overnight and then was recrystallized from a small valume of water. A 220 MHz NMR spectrum established the product to be the desired compound.

470 mg of the ester were suspended in 10 ml dioxane/water (1:1). The dioxane was first purified using an alumina column. The pH was adjusted to 9.0 with NaOH. The air in the flask was replaced by gaseous $N_2$. With constant stirring, 436 mg of di-t-butyldicarbonate was added and the reaction was allowed to proceed at room temperature for 48 hours during which time the pH was maintained at 9.0. All suspended material went into solution within 3 hours. After 48 hours a white solid formed. TLC in $CHCL_2$-MeOH-acetic acid (85:10:5) yielded a single spot (Rf 0.8). The reaction mixture was extracted three times with hexane and the aqueous phase was acidified to pH 3.0 with 2 N HCl and was extracted with three 50 ml portions of ethyl acetate. The organic phase was dried over $MgSO_4$, filtered and concentrated in vacuo. The final product was an oil, the composition of which was verified using 220 MHz NMR.

EXAMPLE 3

Preparation of N-t-Boc-S-gamma-methoxycarbonylpropylcystein

The residue was prepared according to the method of Jost K.: Collect.Czech.Chem.Commun. 36:218, 1971 which is incorporated herein by reference. The N-t-Boc group was added in the same manner as described above for Example 2. Examples 4–8 illustrate the synthesis of some of the vasopressins of this invention. The syntheses in Examples 6 and 7 are novel applications of the solid phase method of synthesis.

EXAMPLE 4 (X=H, Y=S—S, A=L, B=D)

Step A, Preparation of N-t-Boc-D-Ala-$NH_2$-resin

A 1.5 g sample of benzyhydryl-amine HCl resin purchased from Beckman was placed in a 75 ml reaction vessel. Analysis of the resin by the manufacturer indicated 0.47 mEquiv/g available amine. The resin was washed five times with 17 ml 5% N, N'-di-isopropyl-ethyl-amine (DIEA) in methylene chloride ($CH_2Cl_2$) for 0.5 minutes each time (5×0.5 min). A 0.4 g portion of the t-Boc-D-Ala (2.12 mEquiv) in 5 ml $CH_2Cl_2$ was added to the mixture and shaken for 2 minutes. A 5 ml portion of N,N'-dicyclohexyl-carbodiimide (DCC) in $CH_2Cl_2$ (0.42 mEquiv/ml) was added and the reaction mixture was again shaken for 30 minutes. The resin was then washed five times with 25 ml $CH_2Cl_2$ for 0.5 minutes each time, 2 times with 17 ml 2-propanol for 0.5 minutes (2×0.5 min), 25 ml $CH_2Cl_2$ (2×0.5 min). Picric acid monitoring established 99.6% coupling of the residue.

Step B, Preparation of N-t-Boc-Arg (Tosyl)-D-Ala-$NH_2$-resin

The peptide resin from Step A was washed with 25 ml $CH_2Cl_2$ (5×5 min), 25 ml 50% trifluoracetic acid (TFA) in $CH_2Cl_2$ (1×20 min), 25 ml 50% TFA in $CH_2Cl_2$ (1×30 min), 25 ml $CH_2Cl_2$ (5×0.5 min), 17 ml 2-propanol (2×0.5 min) and 25 ml $CH_2Cl_2$ (5×0.5 min). The procedure from Step A after the addition of t-Boc-D-Ala was then repeated, except that 748.6 mg (2.12 mEquiv) of t-Boc-Arg (Tos) in 5 ml 5% N, N-dimethylformamide (DMF) in $CH_2Cl_2$ was used in place of t-Boc-D-Ala. Tos is used herein as an accepted abbreviation for tosyl. Picric acid monitoring established 95.9% coupling of the residue.

Step C, Preparation of N-t-Boc-Pro-Arg(Tos)-D-Ala-$NH_2$-resin

The procedure from Step B above was repeated except that 456 mg (2.12 mEquiv) of t-Boc-Pro in 5 ml $CH_2Cl_2$ was used in place of t-Boc-Arg(Tos). Picric acid monitoring established 93.9% efficiency of coupling of the residue.

Step D, Preparation of N-T-Boc-Cys-(S-p-MeOBzl)-Pro-Arg(Tos)-D-Ala-$NH_2$-resin

The procedure from Step C above was repeated except that 723.4 mg (2.12 mEquiv) of t-Boc-S-p-MeOBzl-Cys (methoxybenzyl=MeOBzl) in 5 ml $CH_2Cl_2$ was used in place of t-Boc-Pro. Picric acid monitoring established 92.8% efficiency of coupling of the residue.

Step E, Preparation of N-t-Boc-Asn-Cys(S-p-MeOBzl)-Pro-Arg(Tos)-D-Ala-$NH_2$-resin The peptide resin from Step D was then washed with 25 ml $CH_2Cl_2$ (5×5 min), 25 ml 50% trifluoracetic acid (TFA) in $CH_2Cl_2$ (1×20 min), 25 ml 50% TFA in $CH_2Cl_2$ (1×30 min), 25 ml $CH_2Cl_2$ (5×0.5 min), 17 ml 2-propanol (2×0.5 min) and 25 ml $CH_2Cl_2$ (5×0.5 min). The resin was then washed with 17 ml 2-propanol (2×0.5 min), 25 ml $CH_2Cl_2$ (5×0.5 min) and 17 ml DMF (0.42 mEquiv/ml) (2×2 min). A solution of 492 mg (2.12 mEquiv) of t-Boc-Asn and 649.3 mg (4.45 mEquiv) of 1-hydroxy-benzotriazole hydrate (HOBzt) in 5 ml DMF (0.42 mEquiv/ml) was added to the resin and shaken for 2 hours. The resin was then washed with 17 ml DMF (1×2 min), 25 ml $CH_2Cl_2$ (5×0.5 min), 17 ml 2-propanol (2×0.5 min) and 25 ml $CH_2Cl_2$ (5×0.5 min).

A second coupling was carried out by repeating all the previous steps in Step D starting with the first DMF wash. Picric acid monitoring established 92.5% efficiency of coupling of the residue.

Step F, Preparation of N-t-Boc-Gln-Asn-Cys(S-p-MeOBzl)-Pro-Arg(Tos)-D-Ala-$NH_2$-resin The procedure for the coupling of this residue was identical to Step E above except that a solution of 521.6 mg (2.12 mEquiv) of t-Boc-Gln and 649.3 mg (4.24 mEquiv) of HOBzt in 5 ml DMF was used. Picric acid monitoring established 90.3% efficiency of coupling of the residue.

Step G, Preparation of N-t-Boc-Phe-Gln-Asn-Cys(S-p-MeOBzl)-Pro-Arg(Tos)-D-Ala-$NH_2$-resin The procedure for coupling of this residue was identical to that for the coupling of t-Boc-Pro in Step C above except that the deprotection time was reduced to 15 min. as opposed to 30 min. in Step C and 562.2 mg (2.12 mEquiv) of t-Boc-Phe in 5 ml $CH_2Cl_2$ was used in place of t-Boc-Pro. Picric acid monitoring established 88.4% efficiency of coupling of the residue.

Step H, Preparation of N-t-Boc-Tyr-Phe-Gln-Asn-Cys(S-p-MeOBzl)-Pro-Arg(Tos)-D-Ala-$NH_2$-resin The procedure for coupling this residue was identical to that in Step C above except that 596 mg (2.12 mEquiv) of of t-Boc-Tyr in 5 ml 5% DMF/$CH_2Cl_2$ was used in place of t-Boc-Pro. Picric acid monitoring showed 87.1% efficiency of coupling. The peptide resin was then washed exhaustively with absolute methanol and air dried. The yield of dry resin was 2.12 g.

Step I, Preparation of S-p-MeBzl-mercaptopropionic acid-Tyr-Phe-Gln-Asn-Cys(S-p-MeOBzl)-Pro-Arg(Tos)-D-Ala-NH$_2$-resin 1.06 g of the product from Step H was returned to the reaction vessel and coupled by the same procedure as in Step C above, except that 221.8 mg (1.06 mEquiv) of S-(4-methoxybenzyl)-beta-mercaptopropionic acid as prepared in Example 1 in 5 ml CH$_2$Cl$_2$ was used in place of t-Boc-Pro. Picric acid monitoring showed 92.5% efficiency of coupling. The peptide resin was then exhaustively washed with absolute methanol and air dried. The yield was 1.10 g (96% based on resin substitution).

Step J, Preparation of 1-Desamino-[9-D-Ala-NH]-arginine-vasopressin

A 500 mg sample of the peptide resin from Step 1 was placed in the 50 ml Teflon-Kel-F vessel of the HF apparatus purchased from Peninsula Laboratories. A small teflon-coated magnetic stirring bar was inserted and 1 ml of anisole was added. A teflon frit was secured near the top of the vessel and the latter was attached to the HF apparatus. The vessel was evacuated with a water aspirator and immersed in a dry ice/acetone bath. After 20 min, the sample vessel was disconnected from the vacuum and connected to the HF reservoir. HF was distilled into the vessel until the liquid volume was about 10 ml. The dry ice/acetone bath was replaced by an ice bath containing a magnetic stirrer and the sample vessel was sealed off from the rest of the system. After 75 min. the vessel was carefully opened to the aspirator and the HF was pulled off through the aspirator. After 30 min., the line was switched to a mechanical pump and pumping continued for 1 hour. The sample vessel remained immersed in a 0° C. bath throughout this period. The system was then filled with Argon until atmospheric pressure had been attained and the vessel was quickly removed and the top was sealed with parafilm.

The material was washed out of the vessel into a course-fritted funnel with about 100 ml of degassed ethyl acetate in several portions. The funnel and vessel were then placed in a large freeze-dryer vessel and the resin in the funnel was then washed with 100 ml of degassed 1 M acetic acid in several portions, followed by 160 ml of degassed water in several portions. The solution was then adjusted to pH 8 with NH$_4$OH and 25 ml of 0.01 M potassium ferricyanide solution was added by drops. The yellow solution was stirred for about 30 min. and the pH was then adjusted to 5.0 with 50% acetic acid. 5 grams AG-3 anion exchange resin (TFA cycle) was added and the mixture stirred for an additional 20 mins. The slurry was then filtered, yielding a clear colorless solution, and the resin was washed with a small portion of water. The solution was then freeze-dried.

The resulting powder was taken up in 20 ml 50% acetic acid and filtered through a Millipore filter, yielding a clear pale yellow solution. The latter was applied to a Sephadex G-15 (2.5 cm × 70 cm) column previously equilibrated with 50% acetic acid. Two peaks of OD$_{280}$ were eluted. Peak 1 retained a slight yellow color and appeared in fractions 18–22. Peak 2 was in fractions 23–27 and represented the desired product. The yield was 32 mg. Amino acid analysis showed: NH$_3$ 2.8, Arg 1.1, Asp 1.0, Glu 0.9, Pro 1.0, Ala 1.1, hemi-Cys 0.8, Tyr 0.8, Phe 0.8 (using performic acid oxide hydrolysis). TLC of the material from the second peak with chloride —O— toluidine reaction revealed (ninhydrin visualization did not reveal any additional spots):

| Solvent system for TLC | Spots | RF |
| --- | --- | --- |
| 1-butanol-acetic acid-water (4:1:5, upper phase) | 1 | 0.31 |
| 1-butanol-acetic acid-pyridine-water (15:3:10:12) | 1 | 0.45 |
| ethyl acetate-pyridine-acetic acid-water (5:5:1:3) | 1 | 0.73 |

EXAMPLE 5 (X=NH$_2$, Y=S-S, A=L, B=D)

Preparation of ([9-D-Ala-NH$_2$]-arginine-vasopressin

All steps were the same as Example 4 except that the peptide-resin from Step H was coupled with t-Boc-S-p-MeOBzl-Cys in Step I. Amino acid analysis; NH$_3$ 3.2, Arg 1.0, Glu 0.9, Pro 1.0, Ala 1.1, hemi-Cys 1.8, Tyr 0.9, Phe 0.9 (performic acid oxide (hydrolysis). The yield was 48 mg of material from the second peak.

EXAMPLE 6 (X=H, Y=CH$_2$S, A=L, B=D)

Preparation of (1-desamino-1 monocarba-[9-D-Ala-NH$_2$]-arginine-vasopressin

All steps were the same as Example 4 except that at Step D the compound from Example 2 was substituted for N-t-Boc-S-P-MeOBzl-Cys and the final coupling of S-(4-MeBzl)-betamercaptopropionic acid in Step I was omitted. The side chain ethyl ester of the residue of Step F was then converted to the N-hydroxysuccinimide ester and the peptide was cyclized in the same manner as in Jost, K.: Collect.Czech.Chem.Commun. 36:218, 1971, incorporated herein by reference. Removal of the cyclic peptide from the resin with the simultaneous removal of the tosyl group from 8-Arg with liquid HF and the final purification of the peptide was as described in Example 4, Step J.

EXAMPLE 7 (X=H, Y=SCH$_2$, A=L, B=D)

Preparation of (1-desamino-6-monocarba[9-D-Ala-NH$_2$]-arginine)-vasopressin

The synthesis was the same as in Example 6, above, except that in Step D instead of the compound from Example 2, the compound from Example 3 was used.

EXAMPLE 8 (X=H, Y=S-S, A=D, B=L)

Preparation of (1-desamino-[8-D-Arg, 9-Ala-NH$_2$]arginine)-vasopressin

The synthesis was the same as in Example 4, except that in Step A N-t-Boc-Ala was coupled to the resin and in Step B N-t-Boc-D-Arg(Tos) was coupled. All other steps were unchanged.

The compounds from Examples 4–8 were tested by intravenously injecting the compounds in physiological saline into a normal dog which was anesthetized using sodium pentothal. Blood samples were withdrawn from each dog after 30, 60 and 120 minutes and tested.

The classic F-VIII clotting assay (c) was carried out on the blood samples using pre-injection blood from each dog as the standard (100%) and pooled canine plasma from hemophiliac dogs as (0%). The F-VIII factor level was also determined by radioimmunoassay(RIA). The results of these tests are reported in Table I. Desmopressin (10 μg/kg) was used as a reference injection peptide. It can be seen that in most cases 10 μg/kg of the novel vasopressin analogs produced as much or more F-VIII than 10 μg/kg desmopressin. However, while both desmopressin and the novel analogs have less than 0.2 IU/mg of pressor activity, the novel analogs have less than 0.2 IU/mg antidiuretic activity as opposed to more than 1000 IU/mg antidiuretic activity for desmopressin.

TABLE I

| Compound | 30' (c) | 30' (RIA) | 60' (c) | 60' (RIA) | 120' (c) | 120' (RIA) |
|---|---|---|---|---|---|---|
| Example 4 | | | | | | |
| 5 μg/kg | 120% | 115% | 160% | 125% | 170% | 130% |
| 10 μg/kg | 230 | 124 | 250 | 132 | 240 | 163 |
| Example 5 | | | | | | |
| 5 μg/kg | 115 | 110 | 120 | 107 | 105 | 98 |
| 10 μg/kg | 225 | 115 | 128 | 110 | 115 | 115 |
| Example 6 | | | | | | |
| 5 μg/kg | 135 | 120 | 185 | 135 | 190 | 145 |
| 10 μg/kg | 210 | 130 | 260 | 140 | 265 | 165 |
| Example 7 | | | | | | |
| 5 μg/kg | 145 | 140 | 190 | 150 | 210 | 155 |
| 10 μg/kg | 240 | 125 | 255 | 165 | 266 | 180 |
| Example 8 | | | | | | |
| 10 μg/kg | 155 | 120 | 150 | 145 | 140 | 155 |
| Desmopressin | | | | | | |
| 10 μg/kg | 220 | 126 | 250 | 134 | 210 | 164 |

The results in Table II show that F-VIII/antidiuretic ratio has been improved by more than $10^3$ using the vasopressin analogs of this invention.

TABLE II

Pressor and Antidiuretic Potencies (peak) pf vasopressin analogs in rats, means ± SEM, IU/mg.

| | Ex. 4 | Ex. 5 | Ex. 6 | Ex. 7 | Ex. 8 | Desmopressin |
|---|---|---|---|---|---|---|
| Pressor Potencies | 0.15 ±0.01 | 0.10 ±0.011 | 0.18 ±0.02 | 0.18 ±0.02 | 0.09 ±0.01 | 0.15 ±0.02 |
| Antidiuretic Potencies | 1.8 ±0.4 | 1.2 ±0.4 | 1.9 ±0.5 | 1.9 ±0.2 | 2.23 ±0.56 | 1100 ±150 |

We claim:

1. A vasopressin analog having the general schematic formula:

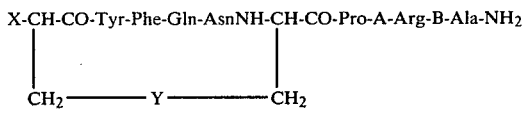

wherein X is selected from the group consisting of H and $NH_2$ and Y is selected from the group consisting of —S—S—, —$CH_2$S— and —S$CH_2$— and A=L when B=D and A=D when B=L.

2. The analog described in claim 1 wherein X is H, Y is S—S, B is D, A is L.

3. The analog described in claim 1 wherein X is $NH_2$, Y is S—S, B is D, A is L.

4. The analog described in claim 1 wherein X is H, Y is $CH_2$S, B is D, A is L.

5. The analog described in claim 1 wherein X is H, Y is S$CH_2$, B is D, A is L.

6. The analog described in claim 1 wherein X is H, Y is S—S, B is L, A is D.

Disclaimer and Dedication

4,285,858.—*Joseph H. Cort,* New York, N.Y. and *Alan Fischman,* New Haven, Conn. VASOPRESSIN ANALOGS. Patent dated Aug. 25, 1981. Disclaimer and Dedication filed July 18, 1983, by the assignee, *Mount Sinai School of Medicine of The City University of New York.*

Hereby disclaims and dedicates to the Public the entire remaining term of said patent.

[*Official Gazette November 1, 1983.*]